(12) United States Patent
Giurgica-Tiron et al.

(10) Patent No.: US 11,069,148 B2
(45) Date of Patent: Jul. 20, 2021

(54) VISUALIZATION OF RECONSTRUCTED HANDSTATE INFORMATION

(71) Applicant: Facebook Technologies, LLC, Menlo Park, CA (US)

(72) Inventors: Tudor Giurgica-Tiron, Stanford, CA (US); Adam Berenzweig, Brooklyn, NY (US); Attila Maczak, Brooklyn, NY (US); Michael Astolfi, Astoria, NY (US); Mason Remaley, Santa Cruz, CA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/258,430

(22) Filed: Jan. 25, 2019

(65) Prior Publication Data

US 2019/0228591 A1 Jul. 25, 2019

Related U.S. Application Data

(60) Provisional application No. 62/621,792, filed on Jan. 25, 2018.

(51) Int. Cl.
*G06T 17/00* (2006.01)
*G06T 19/20* (2011.01)
(Continued)

(52) U.S. Cl.
CPC .............. *G06T 19/20* (2013.01); *G06F 3/014* (2013.01); *G06F 3/015* (2013.01); *G06F 3/016* (2013.01);
(Continued)

(58) Field of Classification Search
CPC .............. G06F 3/015; G06T 13/00–80; G06T 15/00–87; G06T 17/00–30; G06T 19/00–20
See application file for complete search history.

(56) References Cited

U.S. PATENT DOCUMENTS

| 4,055,168 A | 10/1977 | Miller et al. |
| 4,896,120 A | 1/1990 | Kamil |

(Continued)

FOREIGN PATENT DOCUMENTS

| CA | 2902045 A1 | 8/2014 |
| CA | 2921954 A1 | 2/2015 |

(Continued)

OTHER PUBLICATIONS

Hauschild et al., "A Virtual Reality Environment for Designing and Fitting Neural Prosthetic Limbs", 2007, IEEE Transactions on Neural Systems and Rehabilitation Engineering, vol. 15, No. 1, Mar. 2007, pp. 9-15 (Year: 2007).*

(Continued)

*Primary Examiner* — Phong X Nguyen
(74) *Attorney, Agent, or Firm* — FisherBroyles, LLP

(57) ABSTRACT

Method and apparatus for rendering a visual representation based on a musculoskeletal representation. The method comprises updating the musculoskeletal representation based, at least in part, on a plurality of neuromuscular signals recorded from a user, wherein the musculoskeletal representation is updated based at least in part on: position information describing a spatial relationship between two or more connected segments of the musculoskeletal representation, and force information describing a force exerted by at least one segment of the musculoskeletal representation, and rendering, via a user interface, the visual representation based on the updated musculoskeletal representation, wherein the visual representation includes a visual indication of the position information and a visual indication of the force information.

30 Claims, 5 Drawing Sheets

(51) Int. Cl.
  *G06T 15/00* (2011.01)
  *G06F 3/01* (2006.01)
  *G06N 7/00* (2006.01)
  *G06N 20/10* (2019.01)
(52) U.S. Cl.
  CPC ............ *G06F 3/017* (2013.01); *G06N 7/005* (2013.01); *G06N 20/10* (2019.01); *G06T 15/005* (2013.01); *G06T 2219/2012* (2013.01)

(56) References Cited

U.S. PATENT DOCUMENTS

| | | | |
|---|---|---|---|
| 5,625,577 A * | 4/1997 | Kunii | B25J 9/1671 318/561 |
| 5,785,666 A * | 7/1998 | Costello | A61B 5/486 600/595 |
| 6,005,548 A | 12/1999 | Latypov et al. | |
| 6,009,210 A | 12/1999 | Kand | |
| 6,244,873 B1 | 6/2001 | Hill et al. | |
| 6,411,843 B1 | 6/2002 | Zarychta | |
| 6,658,287 B1 | 12/2003 | Litt et al. | |
| 6,720,984 B1 | 4/2004 | Jorgensen et al. | |
| 6,774,885 B1 | 8/2004 | Even-Zohar | |
| 6,942,621 B2 | 9/2005 | Avinash et al. | |
| 7,089,148 B1 | 8/2006 | Bachmann et al. | |
| 7,351,975 B2 | 4/2008 | Brady et al. | |
| 7,574,253 B2 | 8/2009 | Edney et al. | |
| 7,580,742 B2 | 8/2009 | Tan et al. | |
| 7,787,946 B2 | 8/2010 | Stahmann et al. | |
| 7,805,386 B2 | 9/2010 | Greer | |
| 7,853,432 B2 * | 12/2010 | Hero, III | G01N 15/1459 702/181 |
| 7,901,368 B2 | 3/2011 | Flaherty et al. | |
| 8,170,656 B2 | 5/2012 | Tan et al. | |
| 8,190,249 B1 | 5/2012 | Gharieb et al. | |
| 8,311,623 B2 | 11/2012 | Sanger | |
| 8,351,651 B2 | 1/2013 | Lee | |
| 8,421,634 B2 | 4/2013 | Tan et al. | |
| 8,435,191 B2 | 5/2013 | Barboutis et al. | |
| 8,437,844 B2 | 5/2013 | Syed Momen et al. | |
| 8,447,704 B2 | 5/2013 | Tan et al. | |
| 8,484,022 B1 | 7/2013 | Vanhoucke | |
| 8,718,980 B2 | 5/2014 | Garudadri et al. | |
| 8,744,543 B2 | 6/2014 | Li et al. | |
| 8,754,862 B2 | 6/2014 | Zaliva | |
| D717,685 S | 11/2014 | Bailey et al. | |
| 8,880,163 B2 | 11/2014 | Barachant et al. | |
| 8,890,875 B2 | 11/2014 | Jammes et al. | |
| 8,892,479 B2 | 11/2014 | Tan et al. | |
| 9,037,530 B2 | 5/2015 | Tan et al. | |
| D742,272 S | 11/2015 | Bailey et al. | |
| 9,218,574 B2 | 12/2015 | Phillipps et al. | |
| 9,235,934 B2 | 1/2016 | Mandella et al. | |
| 9,240,069 B1 | 1/2016 | Li | |
| 9,278,453 B2 | 3/2016 | Assad | |
| 9,299,248 B2 | 3/2016 | Lake et al. | |
| D756,359 S | 5/2016 | Bailey et al. | |
| 9,351,653 B1 | 5/2016 | Harrison | |
| 9,367,139 B2 | 6/2016 | Ataee et al. | |
| 9,372,535 B2 | 6/2016 | Bailey et al. | |
| 9,387,083 B2 * | 7/2016 | Al Hares | A61F 2/38 |
| 9,389,694 B2 | 7/2016 | Ataee et al. | |
| 9,408,316 B2 | 8/2016 | Bailey et al. | |
| 9,459,697 B2 | 10/2016 | Bedikian et al. | |
| 9,483,123 B2 | 11/2016 | Aleem et al. | |
| 9,597,015 B2 | 3/2017 | McNames et al. | |
| 9,600,030 B2 | 3/2017 | Bailey et al. | |
| 9,612,661 B2 | 4/2017 | Wagner et al. | |
| 9,613,262 B2 | 4/2017 | Holz | |
| 9,654,477 B1 | 5/2017 | Kotamraju | |
| 9,659,403 B1 | 5/2017 | Horowitz | |
| 9,687,168 B2 | 6/2017 | John | |
| 9,690,784 B1 * | 6/2017 | Hughes | G06F 3/0481 |
| 9,696,795 B2 | 7/2017 | Marcolina et al. | |
| 9,720,515 B2 | 8/2017 | Wagner et al. | |
| 9,741,169 B1 | 8/2017 | Holz | |
| 9,766,709 B2 | 9/2017 | Holz | |
| 9,785,247 B1 | 10/2017 | Horowitz et al. | |
| 9,788,789 B2 | 10/2017 | Bailey | |
| 9,864,431 B2 | 1/2018 | Keskin et al. | |
| 9,867,548 B2 | 1/2018 | Le et al. | |
| 9,880,632 B2 | 1/2018 | Ataee et al. | |
| 9,891,718 B2 | 2/2018 | Connor | |
| 9,918,504 B1 * | 3/2018 | Johnson | A61F 13/104 |
| 10,042,422 B2 | 8/2018 | Morun et al. | |
| 10,070,799 B2 | 9/2018 | Ang et al. | |
| 10,078,435 B2 | 9/2018 | Noel | |
| 10,101,809 B2 | 10/2018 | Morun et al. | |
| 10,152,082 B2 | 12/2018 | Bailey | |
| 10,188,309 B2 | 1/2019 | Morun et al. | |
| 10,199,008 B2 | 2/2019 | Aleem et al. | |
| 10,203,751 B2 | 2/2019 | Keskin et al. | |
| 10,216,274 B2 | 2/2019 | Chapeskie et al. | |
| 10,251,577 B2 | 4/2019 | Morun et al. | |
| 10,310,601 B2 | 6/2019 | Morun et al. | |
| 10,331,210 B2 | 6/2019 | Morun et al. | |
| 10,362,958 B2 | 7/2019 | Morun et al. | |
| 10,409,371 B2 | 9/2019 | Kaifosh et al. | |
| 10,437,335 B2 | 10/2019 | Daniels | |
| 10,460,455 B2 | 10/2019 | Giurgica-Tiron et al. | |
| 10,489,986 B2 | 11/2019 | Kaifosh et al. | |
| 10,496,168 B2 | 12/2019 | Kaifosh et al. | |
| 10,504,286 B2 | 12/2019 | Kaifosh et al. | |
| 2003/0144829 A1 | 7/2003 | Geatz et al. | |
| 2003/0171921 A1 | 9/2003 | Manabe et al. | |
| 2003/0184544 A1 | 10/2003 | Prudent | |
| 2004/0054273 A1 | 3/2004 | Finneran et al. | |
| 2004/0068409 A1 * | 4/2004 | Tanaka | G06F 3/015 704/272 |
| 2004/0092839 A1 | 5/2004 | Shin et al. | |
| 2006/0129057 A1 | 6/2006 | Maekawa et al. | |
| 2007/0009151 A1 | 1/2007 | Pittman et al. | |
| 2007/0172797 A1 | 7/2007 | Hada et al. | |
| 2007/0177770 A1 | 8/2007 | Derchak et al. | |
| 2007/0256494 A1 * | 11/2007 | Nakamura | A61B 5/224 73/379.01 |
| 2007/0285399 A1 | 12/2007 | Lund | |
| 2008/0051673 A1 | 2/2008 | Kong et al. | |
| 2008/0052643 A1 | 2/2008 | Ike et al. | |
| 2008/0103639 A1 | 5/2008 | Troy et al. | |
| 2008/0214360 A1 | 9/2008 | Stirling et al. | |
| 2008/0221487 A1 | 9/2008 | Zohar et al. | |
| 2009/0027337 A1 | 1/2009 | Hildreth | |
| 2009/0037507 A1 * | 2/2009 | Rosman | G06F 17/17 708/441 |
| 2009/0079813 A1 | 3/2009 | Hildreth | |
| 2009/0082692 A1 | 3/2009 | Hale et al. | |
| 2009/0082701 A1 * | 3/2009 | Zohar | A61B 5/224 600/595 |
| 2009/0112080 A1 | 4/2009 | Matthews | |
| 2009/0124881 A1 | 5/2009 | Rytky | |
| 2009/0326406 A1 | 12/2009 | Tan et al. | |
| 2009/0327171 A1 | 12/2009 | Tan et al. | |
| 2010/0030532 A1 | 2/2010 | Arora et al. | |
| 2010/0063794 A1 | 3/2010 | Hernandez-Rebollar | |
| 2010/0106044 A1 | 4/2010 | Linderman | |
| 2010/0113910 A1 | 5/2010 | Brauers et al. | |
| 2010/0280628 A1 | 11/2010 | Sankai | |
| 2010/0292595 A1 | 11/2010 | Paul | |
| 2010/0292606 A1 | 11/2010 | Prakash et al. | |
| 2010/0292617 A1 | 11/2010 | Lei et al. | |
| 2010/0293115 A1 | 11/2010 | Seyed Momen | |
| 2010/0315266 A1 | 12/2010 | Gunawardana et al. | |
| 2011/0071417 A1 * | 3/2011 | Liu | G06F 3/011 600/546 |
| 2011/0077484 A1 | 3/2011 | Van Slyke et al. | |
| 2011/0092826 A1 | 4/2011 | Lee et al. | |
| 2011/0173204 A1 | 7/2011 | Murillo et al. | |
| 2011/0173574 A1 | 7/2011 | Clavin et al. | |
| 2011/0230782 A1 | 9/2011 | Bartol et al. | |
| 2012/0066163 A1 | 3/2012 | Balls et al. | |
| 2012/0188158 A1 | 7/2012 | Tan et al. | |
| 2012/0265480 A1 | 10/2012 | Oshima | |
| 2012/0283526 A1 | 11/2012 | Gommesen et al. | |

(56) References Cited

U.S. PATENT DOCUMENTS

| | | |
|---|---|---|
| 2013/0004033 A1 | 1/2013 | Trugenberger |
| 2013/0077820 A1 | 3/2013 | Marais et al. |
| 2013/0123656 A1 | 5/2013 | Heck |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1* | 9/2013 | Tan ........................ G06N 20/00 706/12 |
| 2013/0317382 A1 | 11/2013 | Le |
| 2013/0317648 A1* | 11/2013 | Assad .................... B25J 9/1694 700/258 |
| 2013/0322728 A1* | 12/2013 | Jacobs ................... A61B 5/055 382/132 |
| 2014/0052150 A1* | 2/2014 | Taylor .................... A61B 34/35 606/130 |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1* | 7/2014 | Bailey ...................... G06F 3/011 345/156 |
| 2014/0223462 A1 | 8/2014 | Aimone et al. |
| 2014/0240103 A1 | 8/2014 | Lake et al. |
| 2014/0240223 A1* | 8/2014 | Lake ........................ G06F 3/011 345/156 |
| 2014/0245200 A1 | 8/2014 | Holz |
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0306891 A1* | 10/2014 | Latta .................... G02B 27/017 345/158 |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0075303 A1* | 3/2015 | Connor .................... G06F 3/011 73/865.4 |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0154889 A1* | 6/2015 | Tuchschmid .......... G09B 23/28 434/267 |
| 2015/0157944 A1 | 6/2015 | Gottlieb |
| 2015/0169074 A1 | 6/2015 | Ataee et al. |
| 2015/0182165 A1 | 7/2015 | Miller et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370320 A1* | 12/2015 | Connor ................ A61B 5/1126 345/173 |
| 2015/0370326 A1 | 12/2015 | Chapeskie et al. |
| 2015/0370333 A1* | 12/2015 | Ataee ................... G06K 9/6202 345/156 |
| 2016/0011668 A1 | 1/2016 | Gilad-Bachrach et al. |
| 2016/0049073 A1 | 2/2016 | Lee |
| 2016/0092504 A1 | 3/2016 | Mitri et al. |
| 2016/0140728 A1 | 5/2016 | Aonuma et al. |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0207201 A1* | 7/2016 | Herr ....................... B25J 9/1694 |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1* | 10/2016 | Connor ................... A61B 5/0059 |
| 2016/0313801 A1* | 10/2016 | Wagner ................... G09B 21/02 |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler |
| 2017/0065679 A1* | 3/2017 | Cowburn ................ G06F 3/011 |
| 2017/0068445 A1 | 3/2017 | Lee et al. |
| 2017/0080346 A1 | 3/2017 | Abbas |
| 2017/0090604 A1* | 3/2017 | Barbier .................... G01L 5/226 |
| 2017/0091567 A1 | 3/2017 | Wang et al. |
| 2017/0119472 A1 | 5/2017 | Herrmann et al. |
| 2017/0123487 A1* | 5/2017 | Hazra ....................... G06F 1/163 |
| 2017/0124816 A1 | 5/2017 | Yang et al. |
| 2017/0161635 A1 | 6/2017 | Oono et al. |
| 2017/0188980 A1 | 7/2017 | Ash |
| 2017/0220923 A1* | 8/2017 | Bae ........................ G06K 9/6273 |
| 2017/0259167 A1 | 9/2017 | Cook et al. |
| 2017/0259428 A1* | 9/2017 | Assad ..................... G16H 40/67 |
| 2017/0285755 A1* | 10/2017 | Churchill ............... G06F 3/0481 |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0344706 A1 | 11/2017 | Torres et al. |
| 2017/0347908 A1 | 12/2017 | Watanabe et al. |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1* | 1/2018 | Kaifosh .................. G06F 3/015 345/156 |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1 | 4/2018 | Kerth et al. |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0143696 A1* | 5/2018 | Chen ........................ G01P 13/00 |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0301057 A1 | 10/2018 | Hargrove et al. |
| 2018/0301061 A1* | 10/2018 | Paudyal ................ G09B 21/009 |

(56) References Cited

U.S. PATENT DOCUMENTS

| | | | |
|---|---|---|---|
| 2018/0307314 A1 | 10/2018 | Connor | |
| 2018/0321745 A1 | 11/2018 | Morun et al. | |
| 2018/0321746 A1 | 11/2018 | Morun et al. | |
| 2018/0333575 A1* | 11/2018 | Bouton | A61B 5/4836 |
| 2018/0338720 A1* | 11/2018 | Gupta | G06F 3/015 |
| 2018/0344195 A1 | 12/2018 | Morun et al. | |
| 2018/0360379 A1 | 12/2018 | Harrison et al. | |
| 2019/0008453 A1 | 1/2019 | Spoof | |
| 2019/0025919 A1 | 1/2019 | Tadi et al. | |
| 2019/0033967 A1 | 1/2019 | Morun et al. | |
| 2019/0033974 A1* | 1/2019 | Mu | G06F 3/0308 |
| 2019/0038166 A1 | 2/2019 | Tavabi et al. | |
| 2019/0076716 A1* | 3/2019 | Chiou | G08B 25/016 |
| 2019/0121305 A1 | 4/2019 | Kaifosh et al. | |
| 2019/0121306 A1 | 4/2019 | Kaifosh et al. | |
| 2019/0146809 A1 | 5/2019 | Lee et al. | |
| 2019/0150777 A1 | 5/2019 | Guo et al. | |
| 2019/0172585 A1* | 6/2019 | Mazumder | G16H 50/30 |
| 2019/0192037 A1 | 6/2019 | Morun et al. | |
| 2019/0212817 A1 | 7/2019 | Kaifosh et al. | |
| 2019/0223748 A1 | 7/2019 | Al-natsheh et al. | |
| 2019/0227627 A1 | 7/2019 | Kaifosh et al. | |
| 2019/0228330 A1 | 7/2019 | Kaifosh et al. | |
| 2019/0228533 A1 | 7/2019 | Giurgica-Tiron et al. | |
| 2019/0228579 A1 | 7/2019 | Kaifosh et al. | |
| 2019/0228590 A1 | 7/2019 | Kaifosh et al. | |
| 2019/0247650 A1 | 8/2019 | Tran | |
| 2019/0324549 A1 | 10/2019 | Araki et al. | |
| 2019/0357787 A1 | 11/2019 | Barachant et al. | |
| 2019/0362557 A1 | 11/2019 | Lacey et al. | |
| 2020/0265943 A1* | 8/2020 | Sobinov | G06F 3/015 |

FOREIGN PATENT DOCUMENTS

| | | | |
|---|---|---|---|
| CA | 2939644 | A1 | 8/2015 |
| CN | 1838933 | A | 9/2006 |
| CN | 103777752 | A | 5/2014 |
| CN | 105190578 | A | 12/2015 |
| CN | 106102504 | A | 11/2016 |
| EP | 2 198 521 | B1 | 6/2012 |
| EP | 2 959 394 | A1 | 12/2015 |
| EP | 3 104 737 | A1 | 12/2016 |
| EP | 3 425 481 | A1 | 1/2019 |
| JP | H05-277080 | A | 10/1993 |
| JP | 2005-095561 | A | 4/2005 |
| JP | 2010-520561 | A | 6/2010 |
| JP | 2016-507851 | A | 3/2016 |
| JP | 2017-509386 | A | 4/2017 |
| KR | 2015-0123254 | A | 11/2015 |
| KR | 2016-0121552 | A | 10/2016 |
| KR | 10-1790147 | B1 | 10/2017 |
| NO | 2017/150129 | A1 | 9/2017 |
| WO | WO 2008/109248 | A2 | 9/2008 |
| WO | WO 2009/042313 | A1 | 4/2009 |
| WO | WO 2010/104879 | A2 | 9/2010 |
| WO | WO 2012/155157 | A1 | 11/2012 |
| WO | WO 2014/130871 | A1 | 8/2014 |
| WO | WO 2014/186370 | A1 | 11/2014 |
| WO | WO 2014/194257 | A1 | 12/2014 |
| WO | WO 2014/197443 | A1 | 12/2014 |
| WO | WO 2015/027089 | A1 | 2/2015 |
| WO | WO 2015/073713 | A1 | 5/2015 |
| WO | WO 2015/081113 | A1 | 6/2015 |
| WO | WO 2015/123445 | A1 | 8/2015 |
| WO | WO 2015/199747 | A1 | 12/2015 |
| WO | WO 2016/041088 | A1 | 3/2016 |
| WO | WO 2017/062544 | A1 | 4/2017 |
| WO | WO 2017/092225 | A1 | 6/2017 |
| WO | WO 2017/120669 | A1 | 7/2017 |
| WO | WO 2017/172185 | A1 | 10/2017 |
| WO | WO 2017/208167 | A1 | 12/2017 |
| WO | 2019/147956 | A1 | 8/2019 |

OTHER PUBLICATIONS

Davoodi et al., "Development of a Physics-Based Target Shooting Game to Train Amputee Users of Multijoint Upper Limb Prostheses", 2012, Presence, vol. 21, No. 1, Winter 2012, pp. 85-95 (Year: 2012).*
Yang et al., "Surface EMG-based handgrip force predictions using gene expression programming", 2016, Neurocomputing 207, pp. 568-579 (Year: 2016).*
Crouch et al., "Musculoskeletal model-based control interface mimics physiologic hand dynamics during path tracing task", 2017, J. Neural Eng. 14 036008, pp. 1-11 (Year: 2017).*
Lee et al., Dimensionality Reduction and Clustering on Statistical Manifolds, 2007 (Year: 2007).*
PCT/US2017/043686, Oct. 6, 2017, International Search Report and Written Opinion.
PCT/US2017/043686, Feb. 7, 2019, International Preliminary Report on Patentability.
PCT/US2017/043693, Oct. 6, 2017, International Search Report and Written Opinion.
PCT/US2017/043693, Feb. 7, 2019, International Preliminary Report on Patentability.
PCT/US2017/043791, Oct. 5, 2017, International Search Report and Written Opinion.
PCT/US2017/043791, Feb. 7, 2019, International Preliminary Report on Patentability.
PCT/US2017/043792, Oct. 5, 2017, International Search Report and Written Opinion.
PCT/US2017/043792, Feb. 7, 2019, International Preliminary Report on Patentability.
PCT/US2018/056768, Jan. 15, 2019, International Search Report and Written Opinion.
PCT/US2018/061409, Mar. 12, 2019, International Search Report and Written Opinion.
PCT/US2018/063215, Mar. 21, 2019, International Search Report and Written Opinion.
International Search Report and Written Opinion for International Application No. PCT/US2017/043686 dated Oct. 6, 2017.
International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
Benko et al., Enhancing Input On and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.

(56) References Cited

OTHER PUBLICATIONS

Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Gallina et al., Surface EMG Biofeedback. Surface Electromyography: Physiology, Engineering, and Applications. 2016:485-500.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Li et al., Motor Function Evaluation of Hemiplegic Upper-Extremities Using Data Fusion from Wearable Inertial and Surface EMG Sensors. Sensors. MDPI. 2017;17(582):1-17.
McIntee, A Task Model of Free-Space Movement-Based Geastures. Dissertation. Graduate Faculty of North Carolina State University. Computer Science. 2016. 129 pages.
Naik et al., Source Separation and Identification issues in bio signals: A solution using Blind source seperation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.

International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US19/20065 dated May 16, 2019.
Arkenbout et al., Robust Hand Motion Tracking through Data Fusion of 5DT Data Glove and Nimble VR Kinect Camera Measurements. Sensors. 2015;15:31644-71.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Lee et al., Motion and Force Estimation System of Human Fingers. Journal of Institute of Control, Robotics and Systems. 2011;17(10):1014-1020.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
Mendes et al., Sensor Fusion and Smart Sensor in Sports and Biomedical Applications. Sensors. 2016;16(1569):1-31.
Sartori et al., Neural Data-Driven Musculoskeletal Modeling for Personalized Neurorehabilitation Technologies. IEEE Transactions on Biomedical Engineering. 2016;63(5):879-93.
Extended European Search Report for European Application No. EP 17835111.0 dated Nov. 21, 2019.
Extended European Search Report for European Application No. EP 17835140.9 dated Nov. 26, 2019.
International Search Report and Written Opinion for International Application No. PCT/US2019/037302 dated Oct. 11, 2019.
International Search Report and Written Opinion for International Application No. PCT/US2019/034173 dated Sep. 18, 2019.
International Search Report and Written Opinion for International Application No. PCT/US2019/042579 dated Oct. 31, 2019.
Invitation to Pay Additional Fees for International Application No. PCT/US2019/049094 mailed Oct. 24, 2019.
International Search Report and Written Opinion for International Application No. PCT/US2019/052131 dated Dec. 6, 2019.
International Search Report and Written Opinion for International Application No. PCT/US2019/046351 dated Nov. 7, 2019.
Al-Mashhadany, Inverse Kinematics Problem (IKP) of 6-DOF Manipulator Bgy Locally Recurrent Neural Networks (LRNNs). Management and Service Science (MASS). 2010 International Conference ON, IEEE. Aug. 24, 2010. 5 pages. ISBN: 978-1-4244-5325-2.
Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.
Marcard et al., Sparse Inertial Poser: Automatic 3D Human Pose Estimation from Sparse IMUs. Eurographics. 2017;36(2). 12 pages.
Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].
Wittevrongel et al., Spatiotemporal Beamforming: A Transparent and Unified Decoding Approach to Synchronous Visual Brain-Computer Interfacing. Frontiers in Neuroscience. 2017;11:1-12.

(56) References Cited

OTHER PUBLICATIONS

Zacharaki et al., Spike pattern recognition by supervised classification in low dimensional embedding space. Brain Informatics. 2016;3:73-8. DOI: 10.1007/s40708-016-0044-4.
PCT/US2019/028299, Aug. 9, 2019, International Search Report and Written Opinion.
PCT/US2019/031114, Aug. 6, 2019, Invitation to Pay Additional Fees.
International Search Report and Written Opinion for International Application No. PCT/US2019/028299 dated Aug. 9, 2019.
Invitation to Pay Additional Fees for International Application No. PCT/US2019/031114 mailed Aug. 6, 2019.
Gopura et al., A Human Forearm and wrist motion assist exoskeleton robot with EMG-based fuzzy-neuro control. Proceedings of the 2nd IEEE/RAS-EMBS International Conference on Biomedial Robotics and Biomechatronics. Oct. 19-22, 2008. 6 pages.
Valero-Cuevas et al., Computational Models for Neuromuscular Function. NIH Public Access Author Manuscript. Jun. 16, 2011. 52 pages.
International Preliminary Report on Patentability received for PCT Application Serial No. PCT/US2019/015180 dated Aug. 6, 2020, 8 pages.
PCT/US2019/015134, dated May 15, 2019, International Search Report and Written Opinion.
PCT/US2019/015167, dated May 21, 2019, International Search Report and Written Opinion.
PCT/US2019/015174, dated May 21, 2019, International Search Report and Written Opinion.
PCT/US2019/015238, dated May 16, 2019, International Search Report and Written Opinion.
PCT/US2019/015183, dated May 3, 2019, International Search Report and Written Opinion.
PCT/US2019/015180, dated May 28, 2019, International Search Report and Written Opinion.
PCT/US2019/015244, dated May 16, 2019, International Search Report and Written Opinion.
PCT/US19/20065, dated May 16, 2019, International Search Report and Written Opinion.
EP 17835111.0, dated Nov. 21, 2019, Extended European Search Report.
EP 17835140.9, dated Nov. 26, 2019, Extended European Search Report.
PCT/US2019/034173, dated Sep. 18, 2019, International Search Report and Written Opinion.
PCT/US2019/037302, dated Oct. 11, 2019, International Search Report and Written Opinion.
PCT/US2019/042579, dated Oct. 31, 2019, International Search Report and Written Opinion.
PCT/US2019/046351, dated Nov. 7, 2019, International Search Report and Written Opinion.
PCT/US2019/049094, dated Oct. 24, 2019, Invitation to Pay Additional Fees.
PCT/US2019/052131, dated Dec. 6, 2019, International Search Report and Written Opinion.
Extended European Search Report received for EP Patent Application Serial No. 19743791.6 dated Feb. 23, 2021, 10 pages.

\* cited by examiner

VISUALIZATION OF RECONSTRUCTED HANDSTATE INFORMATION

RELATED APPLICATIONS

This Application claims priority under 35 USC 119(e) of U.S. Provisional Application Ser. No. 62/621,792, filed Jan. 25, 2018, entitled "VISUALIZATION OF RECONSTRUCTED HANDSTATE INFORMATION", which is incorporated by reference in its entirety.

BACKGROUND

In some computer applications that generate representations of the human body, it is desirable for the application to know the spatial positioning, orientation and movement of a user's body to provide a realistic representation of body movement. For example, in a virtual reality (VR) environment, tracking the spatial position of the user's hand enables the application to represent hand motion in the VR environment, which allows the user to interact with (e.g., by grasping or manipulating) virtual objects within the VR environment. Some existing techniques for tracking movements of a user's body using wearable sensors include using information obtained from multiple Inertial Measurement Units (IMUs) affixed to different parts of the user's body, and using external imaging devices (e.g., fixed-position cameras) to reconstruct the position and orientation of parts of the user's body.

SUMMARY

In a virtual reality (VR) environment, "immersion" refers to virtual experiences that are sufficiently convincing such that a user experiences the virtual environment as a realistic proxy for reality and feels immersed in the virtual environment. Realistic graphics rendering and a shifting point of view in response to head movements are some features that contribute to immersion in virtual environments. Similarly, it is appreciated that realistic rendering, kinematics, and environmental interaction of rendered hands (or rendered controllers held in a user's hands) contribute to immersion in a virtual environment, due in part to the role of hands in non-virtual environmental interaction and humans' innate ability to detect natural kinematics of the hand, wrist, and arm. Improved systems for realistic and natural rendering of part of a user's body (e.g., a hand) can improve the immersion of user experiences, as well as those of third-party users in a shared virtual environment.

In some computer applications that generate musculoskeletal representations of the human body, it is appreciated that it is desirable for the application to provide a more realistic representation of body position, movement, and force exerted by one or more portions of a user's body (e.g., a hand). In an example, in the VR environment, tracking the spatial position of the user's hand enables virtually rendering a hand, and rendering that realistically approximates natural kinematics and gestures may enhance immersion for the user in the virtual environment. Although some camera-based systems attempt to track position and movement of a user's body, it is appreciated that such interpretations may be improved by using wearable neuromuscular sensors for physiological measurements and modeling based on human anatomy.

Some embodiments are directed to predicting information about the positioning and movements of portions of a user's arm and/or hand represented as a multi-segment articulated rigid body system with joints connecting the multiple segments of the rigid body system. Signals recorded by wearable neuromuscular sensors placed at locations on the user's body are provided as input to a statistical model trained to predict estimates of the position (e.g., absolute position, relative position, orientation) and forces associated with a plurality of rigid segments in a computer-based musculoskeletal representation associated with a hand when a user performs one or more movements. The combination of position information and force information associated with segments of a musculoskeletal representation associated with a hand is colloquially referred to herein as a "handstate" of the musculoskeletal representation. As a user performs different movements, a trained statistical model interprets neuromuscular signals recorded by the wearable neuromuscular sensors into position and force estimates (handstate information) that are used to update the musculoskeletal representation. As the neuromuscular signals are continuously recorded, the musculoskeletal representation is updated in real time (or near real-time) and a visual representation of a hand (e.g., within a virtual reality environment) is optionally rendered based on the current handstate estimates.

Other embodiments are directed to a computerized system for rendering a visual representation based on a musculoskeletal representation. The system comprises at least one computer processor programmed to update, the musculoskeletal representation based, at least in part, on a plurality of neuromuscular signals recorded from a user, wherein the musculoskeletal representation is updated based at least in part on: position information describing a spatial relationship between two or more connected segments of the musculoskeletal representation, and force information describing a force exerted by at least one segment of the musculoskeletal representation, and render, via a user interface, the visual representation based on the updated musculoskeletal representation, wherein the visual representation includes a visual indication of the position information and a visual indication of the force information.

In one aspect, the at least one computer processor is further programmed to: update in real time the visual representation based on the updated musculoskeletal representation.

In another aspect, updating the visual representation further comprises updating the visual indication of the position information and/or the visual indication of the force information.

In another aspect, updating the visual indication of the force information comprises changing a color of a portion of the visual representation corresponding to the at least one segment of the updated musculoskeletal representation to indicate the force information.

In another aspect, changing the color comprises changing a hue of the color for the portion of the visual representation corresponding to the at least one segment, and wherein the hue is indicative of an amount of force exerted by the at least one segment.

In another aspect, updating the visual indication of the force information comprises changing a scale or size of a portion of the visual representation corresponding to the at least one segment of the updated musculoskeletal representation to indicate the force information.

In another aspect, updating the visual indication of the force information comprises applying at least one visual element to a portion of the visual representation corresponding to the at least one segment of the updated musculoskeletal representation to indicate the force information.

In another aspect, a dimension of the at least one visual element is indicative of an amount of force exerted by the at least one segment.

In another aspect, updating the visual indication of the force information comprises increasing or decreasing a brightness of a portion of the visual representation corresponding to the at least one segment of the updated musculoskeletal representation to indicate the force information.

In another aspect, a degree of increase or decrease in the brightness is indicative of an amount of force exerted by the at least one segment.

In another aspect, the at least one computer processor is further programmed to: output a sound representation indicative of the force information associated with the updated musculoskeletal representation.

In another aspect, the at least one computer processor is further programmed to: execute a computer application that provides a virtual reality environment, and update in real time the visual representation in the virtual reality environment, wherein updating the visual representation further comprises updating the visual indication of the position information and the visual indication of the force information.

In another aspect, the virtual reality environment comprises a virtual object, and updating the visual representation comprises updating the visual representation such that a hand interacts with the virtual object within the virtual reality environment.

In another aspect, updating the visual indication of the force information comprises changing an appearance or dimension of the virtual object, wherein a degree of change of the virtual object indicates an amount of force exerted by the at least one segment when interacting with the virtual object within the virtual reality environment.

In another aspect, interacting with the virtual object comprises an action selected from the group consisting of grasping the virtual object, dropping the virtual object, pushing the virtual object, throwing the virtual object, pulling the virtual object, opening the virtual object, and closing the virtual object.

In another aspect, the at least one computer processor is further programmed to: provide feedback to a user regarding an amount of force exerted by the at least one segment of the musculoskeletal representation.

In another aspect, providing feedback comprises providing haptic feedback indicative of the amount of force exerted by the at least one segment.

Other embodiments are directed to a method for rendering a visual representation based on a musculoskeletal representation. The method comprises updating the musculoskeletal representation based, at least in part, on a plurality of neuromuscular signals recorded from a user, wherein the musculoskeletal representation is updated based at least in part on: position information describing a spatial relationship between two or more connected segments of the musculoskeletal representation, and force information describing a force exerted by at least one segment of the musculoskeletal representation; and rendering, via a user interface, the visual representation based on the updated musculoskeletal representation, wherein the visual representation includes a visual indication of the position information and a visual indication of the force information.

In one aspect, the visual representation in a virtual reality environment is updated in real time, wherein updating the visual representation further comprises updating the visual indication of the position information and the visual indication of the force information.

Other embodiments are directed to a computer-readable medium encoded with a plurality of instructions that, when executed by at least one computer processor performs a method. The method comprises updating the musculoskeletal representation based, at least in part, on a plurality of neuromuscular signals recorded from a user, wherein the musculoskeletal representation is updated based at least in part on: position information describing a spatial relationship between two or more connected segments of the musculoskeletal representation, and force information describing a force exerted by at least one segment of the musculoskeletal representation; and rendering, via a user interface, the visual representation based on the updated musculoskeletal representation, wherein the visual representation includes a visual indication of the position information and a visual indication of the force information.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIG. 5A illustrates a wearable portion of the computer-based system and FIG. 5B illustrates a dongle portion connected to a computer, wherein the dongle portion is configured to communicate with the wearable portion.

DETAILED DESCRIPTION

Figure 1:
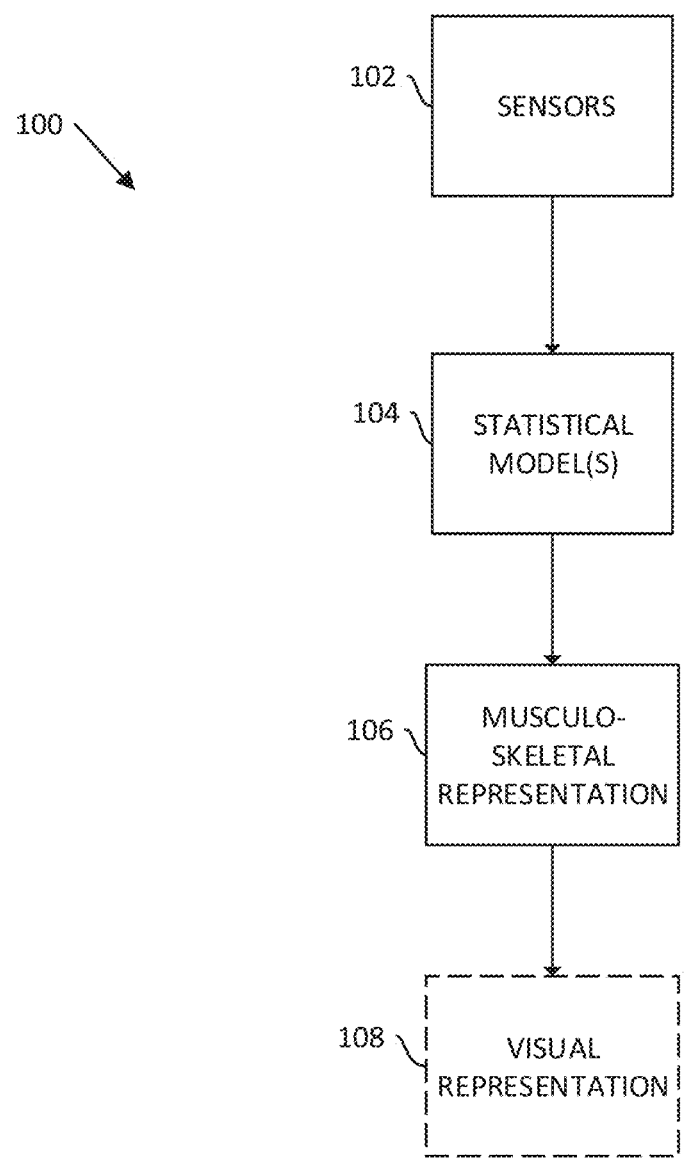
FIG. 1 is a schematic diagram of a computer-based system for reconstructing handstate information in accordance with some embodiments of the technology described herein.

All or portions of the human musculoskeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, a multi-segment articulated rigid body system is used to model portions of the human musculoskeletal system. However, it should be appreciated that some segments of the human musculoskeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the hand may be modeled as a multi-segment articulated body with the joints in the wrist and each finger forming the interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained statistical model, as described in more detail below.

The portion of the human body approximated by a musculoskeletal representation as described herein as one non-limiting example, is a hand or a combination of a hand with one or more arm segments and the information used to describe a current state of the positional relationships between segments and force relationships for individual segments or combinations of segments in the musculoskeletal representation is referred to herein as the handstate of the musculoskeletal representation. It should be appreciated, however, that the techniques described herein are also applicable to musculoskeletal representations of portions of the body other than the hand including, but not limited to, an arm, a leg, a foot, a torso, a neck, or any combination of the foregoing.

In addition to spatial (e.g., position/orientation) information, some embodiments are configured to predict force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when segments in the wrist or fingers are twisted or flexed. In some embodiments, the force information determined as a portion of a current handstate estimate includes one or more of pinching force information, grasping force information, or information about co-contraction forces between muscles represented by the musculoskeletal representation.

FIG. 1 illustrates a system 100 in accordance with some embodiments. The system includes a plurality of sensors 102 configured to record signals resulting from the movement of portions of a human body. Sensors 102 may include autonomous sensors. As used herein, the term "autonomous sensors" refers to sensors configured to measure the movement of body segments without requiring the use of external devices. In some embodiments, sensors 102 may also include non-autonomous sensors in combination with autonomous sensors. As used herein, the term "non-autonomous sensors" refers to sensors configured to measure the movement of body segments using external devices. Examples of external sensors used in non-autonomous sensors include, but are not limited to, wearable (e.g. body-mounted) cameras, global positioning systems, and laser scanning systems.

Autonomous sensors may include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the autonomous sensors includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to a statistical model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon may be used to predict musculoskeletal position information for movements that involve multiple parts of the body.

In some embodiments, sensors 102 only includes a plurality of neuromuscular sensors (e.g., EMG sensors). In other embodiments, sensors 102 includes a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

System 100 also includes one or more computer processors (not shown in FIG. 1) programmed to communicate with sensors 102. For example, signals recorded by one or more of the sensors may be provided to the processor(s), which may be programmed to execute one or more machine learning techniques that process signals output by the sensors 102 to train one or more statistical models 104, and the trained (or retrained) statistical model(s) 104 may be stored for later use in generating a musculoskeletal representation 106, as described in more detail below. Non-limiting examples of statistical models that may be used in accordance with some embodiments to predict handstate information based on recorded signals from sensors 102 are discussed in detail below.

System 100 also optionally includes a display controller configured to display a visual representation 108 (e.g., of a hand). As discussed in more detail below, one or more computer processors may implement one or more trained statistical models configured to predict handstate information based, at least in part, on signals recorded by sensors 102. The predicted handstate information is used to update the musculoskeletal representation 106, which is then optionally used to render a visual representation 108 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained statistical model to accurately represent an intended handstate.

In some embodiments, a computer application configured to simulate a virtual reality environment may be instructed to display a visual representation of the user's hand. Positioning, movement, and/or forces applied by portions of the hand within the virtual reality environment may be displayed based on the output of the trained statistical model(s). The visual representation may be dynamically updated based on current reconstructed handstate information as continuous signals are recorded by the sensors 102 and processed by the trained statistical model(s) 104 to provide an updated computer-generated representation of the user's movement, position, and/or force that is updated in real-time.

As discussed above, some embodiments are directed to using a statistical model for predicting musculoskeletal information based on signals recorded from wearable autonomous sensors. The statistical model may be used to predict the musculoskeletal position information without having to place sensors on each segment of the rigid body that is to be represented in the computer-generated musculoskeletal representation. As discussed briefly above, the types of joints between segments in a multi-segment articulated rigid body model constrain movement of the rigid body. Additionally, individuals tend to move in characteristic ways when performing a task that can be captured in statistical patterns of user behavior (e.g., statistical patterns associated with user-specific characteristics and/or universal characteristics generalized over a population of users). At least some of these constraints on human body movement may be explicitly incorporated into statistical models used for prediction in accordance with some embodiments. Additionally or alternatively, the constraints may be learned by the statistical model though training based on recorded sensor data. Constraints imposed in the construction of the statistical model are those set by anatomy and the physics of a user's body, while constraints derived from statistical patterns are those set by human behavior for one or more users from which sensor measurements are measured. As described in detail below, the constraints may comprise part of the statistical model itself being represented by information (e.g., connection weights between nodes) in the model.

As discussed above, some embodiments are directed to using a statistical model for predicting handstate information to enable the generation and/or real-time update of a computer-based musculoskeletal representation. The statistical model may be used to predict the handstate information based on IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more movements.

Figure 2:
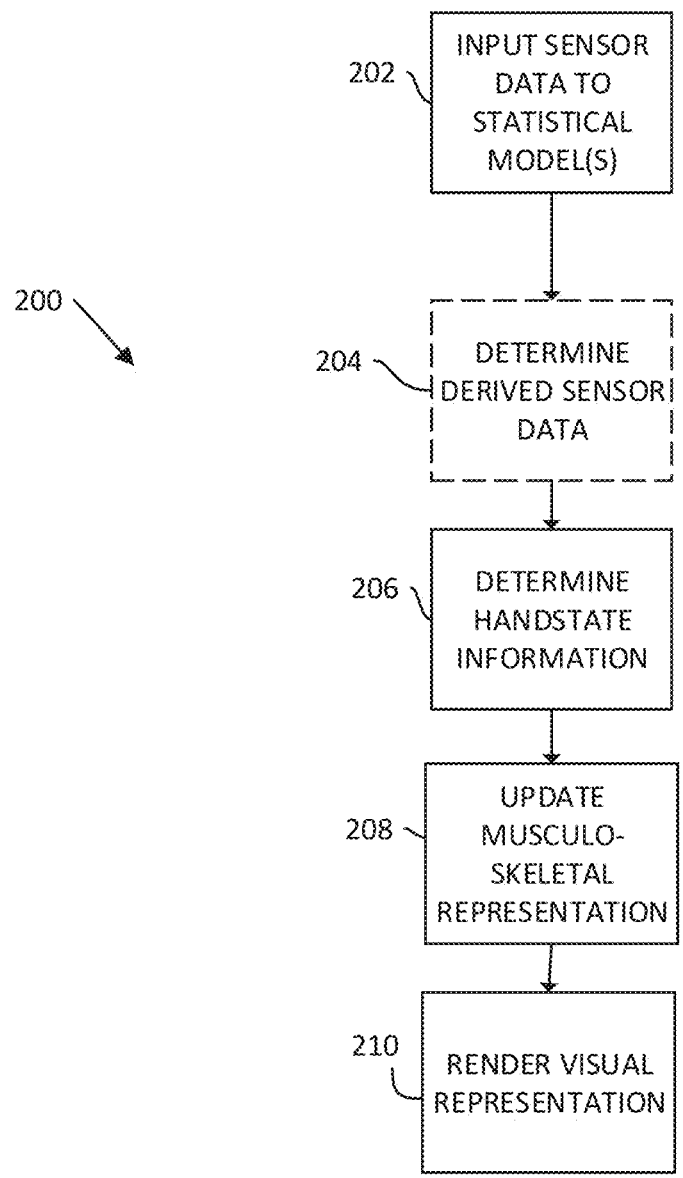
FIG. 2 is a flowchart of a process for determining handstate information in accordance with some embodiments of the technology described herein.

FIG. 2 illustrates a process 200 for determining handstate information based on recorded sensor data in accordance with some embodiments. In act 202, sensor data recorded by one or more sensors is provided as input to one or more trained statistical models used to generate estimates of handstate information, as described briefly above. In some embodiments, the sensors include a plurality of neuromuscular sensors (e.g., EMG sensors) arranged on a wearable device worn by a user. For example, EMG sensors may be arranged on an elastic band configured to be worn around a wrist or forearm of the user to record neuromuscular signals from the user as the user performs various movements or gestures. An example wearable device that may be used in accordance with some embodiments is shown and described in FIGS. 4A and 4B, which are described in more detail below.

As used herein, the term "gestures" refers to a static or dynamic configuration of one or more body parts including the position of the one or more body parts and forces associated with the configuration. For example, gestures include discrete gestures, such as pressing the palm of a hand down on a solid surface or grasping a ball, continuous gestures, such as a waving a finger back and forth or throwing a ball, or a combination of discrete and continuous gestures such as grasping and throwing a ball. Gestures may be defined by an application configured to prompt a user to perform the gestures or, alternatively, gestures may be arbitrarily defined by a user. In some cases, hand and arm gestures may be symbolic and used to communicate according to cultural standards.

In addition to a plurality of neuromuscular sensors, some embodiments include one or more auxiliary sensors configured to continuously record auxiliary signals that may also be provided as input to the one or more trained statistical models. Examples of auxiliary sensors include IMU sensors, imaging devices, radiation detection devices (e.g., laser scanning devices), heart rate monitors, or any other type of biosensors configured to continuously record biophysical information from the user during performance of one or more movements or gestures.

Process 200 then proceeds to act 204, where derived signal data is optionally determined based on the signals recorded by the sensors. For example, accelerometer data recorded by one or more IMU sensors may be integrated and/or filtered to determine derived signal data associated with one or more muscles during performance of a gesture. The derived signal data may be provided as input to the trained statistical model(s) in addition to or as an alternative to raw signal data or otherwise processed raw signal data recorded by the sensors.

Process 200 then proceeds to act 206, where handstate information is determined based on the output of the trained statistical model(s). The gestures performed by the user include discrete gestures, such as placing the hand palm down on a table, and continuous gestures, such as waving a finger back and forth. The gestures performed by the user may include symbolic gestures (e.g., gestures mapped to other gestures, interactions, or commands, for example, based on a gesture vocabulary that specifies the mapping). Some symbolic gestures are meaningful in culturally-specific contexts, and such gestures may be optimized for identification by the trained statistical model and accurately rendered in a virtual environment in order to enhance the immersion of a virtual environment. Communicative symbolic gestures may differ between cultures, and in some embodiments the system may comprise modules that either automatically or upon user selection define a set of appropriate culturally-specific gestures for a particular user. A module that defines a set of culturally-specific gestures may be optimized or otherwise configured for identifying such gestures accurately (and, if appropriate, with low latency) and rendering such gestures with high fidelity.

The neuromuscular signals are recorded continuously during user movements including during performance of the gesture and are provided continuously as input to the trained statistical model, resulting in real-time estimation of the positions and/or forces of the user's hand (i.e., handstate information) as output of the trained statistical model(s). Process 200 then proceeds to act 208, where the real-time handstate estimates output from the trained statistical model(s) are used to update a musculoskeletal representation associated with a hand. In some embodiments, the musculoskeletal representation represents rigid segments within a hand and the joints connecting the rigid segments. In other embodiments, the musculoskeletal representation includes at least some rigid segments corresponding to an arm connected to the hand. Accordingly, the phrase "musculoskeletal representation associated with hand" should be understood to include both musculoskeletal representations of the hand and musculoskeletal representations that include a representation of the hand and at least a portion of an arm connected to the hand.

Process 200 then proceeds to act 210, where a visual representation of a hand is rendered within a graphical user interface based on the updated musculoskeletal representation of the hand. As described above, real-time estimates of the positions and/or forces of the user's hand (e.g., handstate information) output from the trained statistical model(s) are used to update the musculoskeletal representation of the hand. The real-time position and/or force information reflected in the updated musculoskeletal representation of the hand may in turn be depicted in the visual representation of the hand. For example, the visual representation of the hand may include a visual indication of the position information and a visual indication of the force information. The visual indications associated with the position and/or force information may be updated in real-time based on the updated musculoskeletal representation. For example, force information may be represented as a change in the color, size, shape, or other characteristic of all or part of a rendering of a user's body part (e.g. a hand). In another non-limiting example, force information may be represented in a continuous manner by continuously scaling a visual indicator of force (e.g. by adjusting the hue of a visual indicator of force or by scaling all or part of a user's virtually-rendered hand as force increases) or in a categorical manner which may include one or more force thresholds that, once reached, cause the system to display a different visual effect (e.g., sparks coming out of the fingers of a virtually rendered hand).

In some implementations, the visual indication of the force information may be displayed separate from the visual representation of a part of the user's body (e.g., the hand) within the user interface. In other words, the visual indication of the force information may not be overlaid on or be part of the visual representation of a part of the user's body (e.g., the hand). In such implementations, the visual indication of the force information may be rendered/displayed in any of a number of ways. For example, the visual indication of the force information may be displayed near the visual representation of the hand, e.g., as a loading bar (or other graphical element) that indicates the force information (e.g., an amount or strength of force exerted by the hand and/or fingers). The visual indication of the force information may be displayed in a fixed position in the user interface or may be movable next to and together with the visual representation of the hand (e.g., in a virtual reality environment).

In some implementations, the visual representation of the hand may be rendered to represent a realistic hand (e.g., with fingers, joints, palm, etc.). Alternatively, the visual representation of the hand may be rendered as an abstract visual representation of one or more portions of the hand. For example, the fingers in the visual representation may be rendered as circles or the visual representation of the hand may be depicted as an abstract cursor such as a geometrical shape.

In some embodiments, the visual indications of the position and/or force information may be updated by changing a color of a portion of the visual representation of the hand to indicate the position and/or force information. The updated portion of the visual representation may correspond to one or more segments of the updated musculoskeletal representation of the hand to which the position and/or force information relates. For example, when a user performs a "thumbs up" gesture, the force information associated with the fingers may be depicted in the visual representation of the hand. In some implementations, changing the color of the portion of the visual representation of the hand may include changing one or more properties of the color to indicate, for example, an amount of force exerted by the one or more segments. The properties of the color may include, but are not limited to, hue, tint, shade, saturation, and/or other properties. In the example above, different fingers may be depicted with different hues of the same or different color to indicate the amount of force exerted by each finger.

According to one embodiment, the visual indications of the position and/or force information may be updated by changing a scale or size of the portion of the visual representation of the hand corresponding to the one or more segments of the updated musculoskeletal representation of the hand to indicate the position and/or force information. In some implementations, the scale or size of the portion of the visual representation of the hand may be increased or decreased with respect to other portions of the visual representation to indicate the force information. For example, when a user performs a gesture of pressing a finger down on a table, the size of the finger may be increased or decreased to indicate an amount of force exerted by the finger when performing this gesture. When the user changes the orientation of the finger and increases the force by which he presses the finger down on the table, the visual representation of the finger may be dynamically updated to reflect the changed orientation and the increased force exerted by the finger (e.g., by increasing the size or changing the color of the finger).

In another embodiment, the visual indications of the position and/or force information may be updated by applying at least one visual element (e.g., a 2D or 3D visual element) to a portion of the visual representation of the hand that corresponds to one or more segments of the updated musculoskeletal representation of the hand associated with the position and/or force information. For example, circles may be depicted around the one or more segments, where a dimension of each of the circles indicates an amount of force exerted by each segment. In the above example of a user pressing a finger down on the table, a circle or other visual element may be depicted on the visual representation of the finger to indicate force information, and the size of the circle may be increased or decreased in real-time as the user increases or decreases the amount of force exerted by the finger.

In another embodiment, the visual indications of the position and/or force information may be updated by increasing or decreasing a brightness of the portion of the visual representation of the hand corresponding to the one or more segments of the updated musculoskeletal representation of the hand to indicate the position and/or force information. In some implementations, a degree of increase or decrease in the brightness may be indicative of the amount of force exerted by the one or more segments. Continuing with the same example above, the brightness of the finger pressing down on the table may be increased or decreased based on the increased or decreased force exerted by the finger.

It will be appreciated that while certain types of visual indications or effects are described herein, other types of visual indications/effects, such as, a sparkle effect, a glare effect, and/or other visual effects may be used (alternatively or in combination with the visual indications described herein) without departing from the scope of this disclosure. In addition, in some implementations, a visual representation (e.g., associated with hand) may be combined with a sound representation and/or haptic representation indicative of the position and/or force information.

As described above, the visual representation of the hand may be rendered in a virtual reality environment. Positioning, movement, and/or forces applied by portions of the hand may be visually depicted and dynamically updated within the virtual reality environment (e.g., as the user performs a gesture or interacts with virtual objects with the environment). For example, the visual representation may be updated such that the hand interacts with the virtual object within the virtual reality environment and the visual indications of the position and/or force information may be updated to reflect the interaction. Interactions with a virtual object may include one or more actions such as, grasping the virtual object, pushing the virtual object, dropping the virtual object, throwing the virtual object, pulling the virtual object, opening the virtual object, closing the virtual object, and/or other actions.

In some embodiments, the visual indications of the position and/or force information associated with the interactions of the virtual objects may be updated using any or a combination of the techniques described above such as, changing the color, scale, size, and/or brightness associated with the segments, applying visual elements to the segments, generating an auditory representation, generating a haptic representation, etc.

In other embodiments, the visual indications of the position and/or force information associated with the interactions of the virtual objects may be updated by changing an appearance or dimension of the virtual objects. In some implementations, a degree of change in the appearance or dimension of the virtual object may be indicative of an amount of force exerted by the segments when interacting with the virtual object. For example, when the user's interaction with a virtual object, such as a ball, includes grasping the ball, the appearance of the ball may be changed by depicting the ball in a compressed state and/or a dimension of the ball (e.g., the diameter of the ball) may be changed. The degree of compression or size reduction may reflect the amount of force exerted by the user's fingers when grasping the ball.

According to some embodiments, in addition to the visual indications of the position and/or force information, the rendered visual representation may include visual indications of one or more personal characteristics of the user that may, for example, relate to the position and/or force exerted by the segments. For example, a user may have stiffness in particular fingers of the hand that may affect the force with which the user can grasp the ball. Due to the stiffness in the user's fingers, the amount of force indicated in the visual representation of the hand may not be representative of an actual amount of force exerted by the user when grasping the ball. However, by including a visual indication of the stiffness in addition to the visual indications of the force information, the user can readily appreciate the reason for the discrepancy between the force information indicated in the visual representation and the actual amount of force exerted by the user.

In some embodiments, when a user performs a continuous gesture or movement in the virtual reality environment, for example, throwing a ball, the visual indications of the position and/or force information may be updated to reflect the changes in position/orientation of the user's fingers/hand while throwing the ball and/or the changes in the amount of force exerted by the fingers while throwing the ball. In some implementations, the visual representation may include trails representing motion. For example, the trails may be associated with all or a portion (e.g., one or more fingers) of the visual representation of the hand and may be dynamically updated to indicate movements. Alternatively, the trails may be associated with an object with which the visual representation of the hand is interacting during performance of a gesture (e.g., a ball as the user throws the ball) in the virtual reality environment.

As discussed above, the visual representation of the hand may be rendered based on the musculoskeletal representation updated using the current handstate estimates output from the trained statistical model. In some embodiments, the visual representation may be rendered based on an altered version of the musculoskeletal representation. For example, when performing a gesture that includes an interaction with a virtual object in the virtual reality environment, the visual representation of the hand may be rendered to appear distorted to appear closer to a natural pose associated with the interaction. Additionally or alternatively, the visual representation of the hand may include visual cues that highlight various interaction modes. For example, a halo (e.g., rendered in a particular color) may be displayed around the hand, where the presence or absence of the halo and/or the color or other visual aspect of the halo may provide feedback regarding whether the hand is in a correct or incorrect position for a particular interaction with a virtual object.

According to some embodiments, feedback may be provided to the user or a third-party in a shared virtual environment regarding the position and/or force information. For example, feedback may be provided regarding the amount of force exerted by one or more segments of the updated musculoskeletal representation. In some implementations, haptic feedback that is indicative of the amount of force exerted by the segments may be provided to the user or a third-party. In some implementations, the haptic feedback may be provided via the wearable devices described herein (e.g. an elastic band with a plurality of neuromuscular sensors are arranged thereon). In other implementations, the one or more computer processors may be communicatively coupled to a separate wearable device (e.g., a smartwatch) and may be configured to control the separate wearable device to provide the haptic feedback.

According to some embodiments, position and/or force information about a part of a first user's body (e.g. hand) is rendered in a shared virtual environment wherein a third-party in the shared virtual environment experiences a spatially-consistent point of view of the part of the first user's body (e.g. hand) that provides a co-embodied immersive experience for the plurality of user's in a shared virtual environment due to the realistic representation of the part of the first user's body (e.g. hand). Providing a visual representation of a first user's hand position that is rendered with the spatial viewpoint of a third-party in a shared virtual environment contributes to a realistic and more immersive experience for all users in the shared virtual environment. In some embodiments, providing a visual indicator of force exerted, for example, during a gesture performed by the first user or as the first user interacts with various objects, in the shared virtual environment further enhances the immersive experience.

In some implementations, force exerted by a user may be provided as a parameter in a machine control scheme (e.g., to control or manipulate other devices in a virtual environment, such as a surgical robot) and/or may be beneficial to communicate or provide as feedback to the user or third party. For example, the system may be configured to provide a visual indicator to the user (or a third party) concerning a specific force (or force within a range of forces) so that the user may generate an effective force for a particular machine control scheme. Providing feedback about a user's handstate (including force and position information) may be beneficial for various applications (e.g., a remote training application). In one non-limiting example, an industrial equipment technician may enter a virtual environment with a trainee and provide training information to the trainee comprising both handstate position information and a force exerted (e.g., to communicate an appropriate force to exert during use of a particular tool).

Culturally-significant gestures are generally symbolic and may be used to communicate to a third-party who is able to observe the gesture. Accurate rendering of common and/or culturally-significant gestures may enhance the immersion of a virtual environment for a user or a third-party whose virtual point-of-view incorporates the handstate of the user. In some embodiments, a statistical model may be optimized to identify a culturally-significant gesture intended for communication to a third-party (e.g. in a shared virtual environment). By identifying culturally-significant gestures and rendering them (in some cases with a visual and/or other sensory (e.g., auditory, haptic, etc.) signal indicating force), a user and others in a multiplayer shared virtual environment may experience enhanced immersion. Moreover, rendering of a part of the user's body (e.g. hand) may be configured to have reduced dimensionality (e.g., by selecting an appropriate sub-manifold) to improve model accuracy, latency, and/or breadth communication. In some embodiments, a statistical model optimized for use in symbolic gesture communication may be configured to select a sub-manifold to reduce the dimensionality of model outcomes and thus render symbolic and culturally-significant gestures more reliably. In some embodiments, a statistical model configured to detect (and, optionally, render in a virtual environment) a position, movement, and/or force of a part of a user's body may detect and filter out culturally insignificant gestures. In some embodiments, culturally insignificant gestures may be filtered by refraining to display or render such gestures in the virtual environment.

It will be appreciated techniques described herein may be used to identify and accurately render culturally-significant poses (or other means of non-verbal communication) in a shared virtual environment without departing from the scope of this disclosure.

Figure 3:
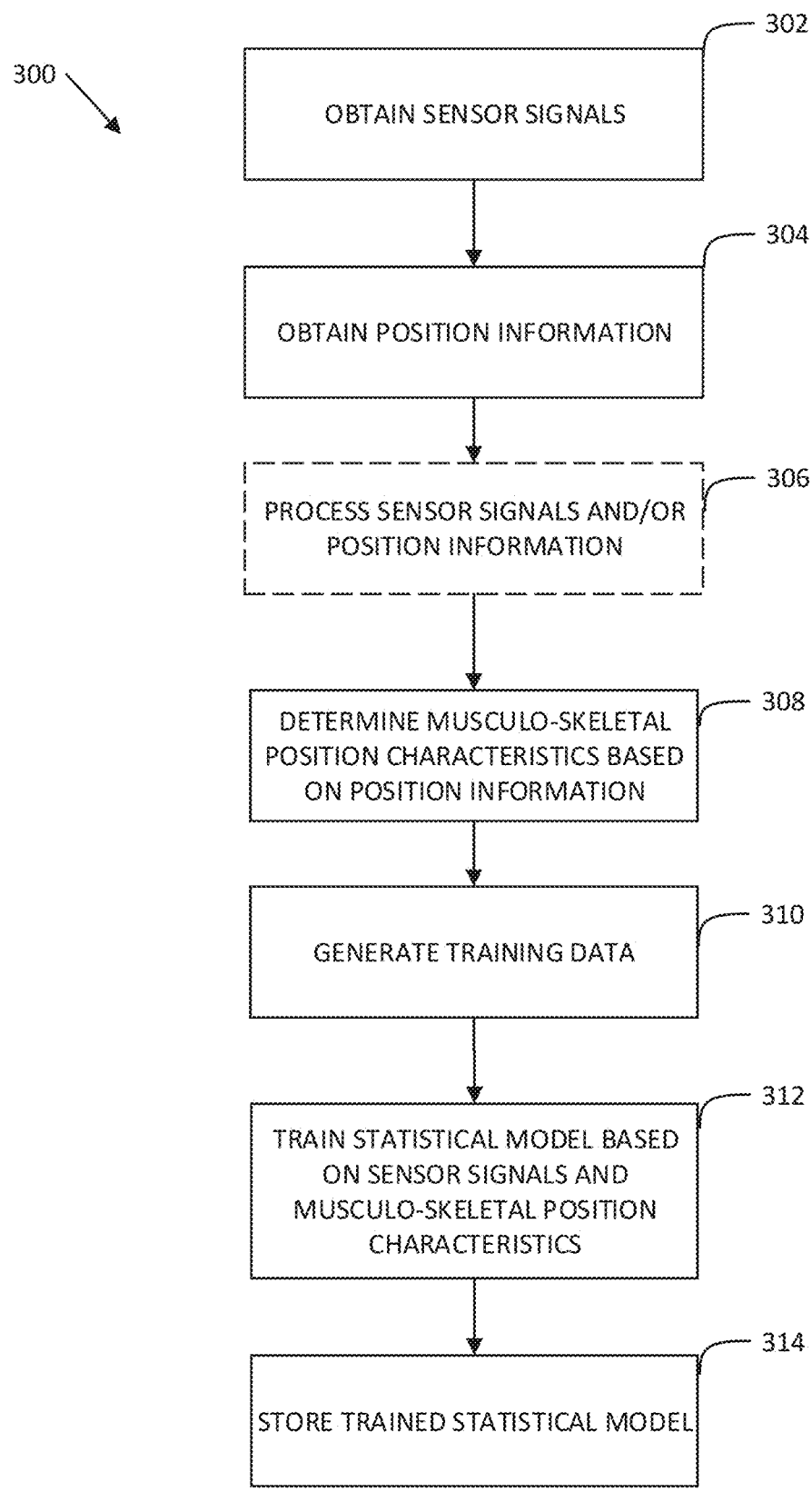
FIG. 3 is a flowchart of a process for generating a statistical model for predicting musculoskeletal position information using signals recorded from sensors, in accordance with some embodiments of the technology described herein.

FIG. 3 describes a process 300 for generating (sometimes termed "training" herein) a statistical model using signals recorded from sensors 102. Process 300 may be executed by any suitable computing device(s), as aspects of the technology described herein are not limited in this respect. For example, process 300 may be executed by one or more computer processors described with reference to FIGS. 5A and 5B. As another example, one or more acts of process 300 may be executed using one or more servers (e.g., servers included as a part of a cloud computing environment). For example, at least a portion of act 310 relating to training of a statistical model (e.g., a neural network) may be performed using a cloud computing environment.

Process 300 begins at act 302, where a plurality of sensor signals are obtained for one or multiple users performing one or more movements (e.g., typing on a keyboard). In some embodiments, the plurality of sensor signals may be recorded as part of process 300. In other embodiments, the plurality of sensor signals may have been recorded prior to the performance of process 300 and are accessed (rather than recorded) at act 302.

In some embodiments, the plurality of sensor signals may include sensor signals recorded for a single user performing a single movement or multiple movements. The user may be instructed to perform a sequence of movements for a particular task (e.g., opening a door) and sensor signals corresponding to the user's movements may be recorded as the user performs the task he/she was instructed to perform. The sensor signals may be recorded by any suitable number of sensors located in any suitable location(s) to detect the user's movements that are relevant to the task performed. For example, after a user is instructed to perform a task with the fingers of his/her right hand, the sensor signals may be recorded by multiple neuromuscular sensors circumferentially (or otherwise) arranged around the user's lower right arm to detect muscle activity in the lower right arm that give rise to the right hand movements and one or more IMU sensors arranged to predict the joint angle of the user's arm relative to the user's torso. As another example, after a user is instructed to perform a task with his/her leg (e.g., to kick an object), sensor signals may be recorded by multiple neuromuscular sensors circumferentially (or otherwise) arranged around the user's leg to detect muscle activity in the leg that give rise to the movements of the foot and one or more IMU sensors arranged to predict the joint angle of the user's leg relative to the user's torso.

In some embodiments, the sensor signals obtained in act 302 correspond to signals from one type of sensor (e.g., one or more IMU sensors or one or more neuromuscular sensors) and a statistical model may be trained based on the sensor signals recorded using the particular type of sensor, resulting in a sensor-type specific trained statistical model. For example, the obtained sensor signals may comprise a plurality of EMG sensor signals arranged around the lower arm or wrist of a user and the statistical model may be trained to predict musculoskeletal position information for movements of the wrist and/or hand during performance of a task such as grasping and twisting an object such as a doorknob.

In embodiments that provide predictions based on multiple types of sensors (e.g., IMU sensors, EMG sensors, MMG sensors, SMG sensors), a separate statistical model may be trained for each of the types of sensors and the outputs of the sensor-type specific models may be combined to generate a musculoskeletal representation of the user's body. In other embodiments, the sensor signals obtained in act 302 from two or more different types of sensors may be provided to a single statistical model that is trained based on the signals recorded from the different types of sensors. In one illustrative implementation, an IMU sensor and a plurality of EMG sensors are arranged on a wearable device configured to be worn around the forearm of a user, and signals recorded by the IMU and EMG sensors are collectively provided as inputs to a statistical model, as discussed in more detail below.

In some embodiments, the sensor signals obtained in act 302 are recorded at multiple time points as a user performs one or multiple movements. As a result, the recorded signal for each sensor may include data obtained at each of multiple time points. Assuming that n sensors are arranged to simultaneously measure the user's movement information during performance of a task, the recorded sensor signals for the user may comprise a time series of K n-dimensional vectors $\{x_k | 1 < k < K\}$ at time points $t_1, t_2, \ldots, t_K$ during performance of the movements.

In some embodiments, a user may be instructed to perform a task multiple times and the sensor signals and position information may be recorded for each of multiple repetitions of the task by the user. In some embodiments, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task he/she was instructed to perform. When sensor signals are collected by multiple users which are combined to generate a statistical model, an assumption is that different users employ similar musculoskeletal positions to perform the same movements. Collecting sensor signals and position information from a single user performing the same task repeatedly and/or from multiple users performing the same task one or multiple times facilitates the collection of sufficient training data to generate a statistical model that can accurately predict musculoskeletal position information associated with performance of the task.

In some embodiments, a user-independent statistical model may be generated based on training data corresponding to the recorded signals from multiple users, and as the system is used by a user, the statistical model is trained based on recorded sensor data such that the statistical model learns the user-dependent characteristics to refine the prediction capabilities of the system for the particular user.

In some embodiments, the plurality of sensor signals may include signals recorded for a user (or each of multiple users) performing each of multiple tasks one or multiple times. For example, a user may be instructed to perform each of multiple tasks (e.g., grasping an object, pushing an object, and pulling open a door) and signals corresponding to the user's movements may be recorded as the user performs each of the multiple tasks he/she was instructed to perform. Collecting such data may facilitate developing a statistical model for predicting musculoskeletal position information associated with multiple different actions that may be taken by the user. For example, training data that incorporates musculoskeletal position information for multiple actions may facilitate generating a statistical model for predicting which of multiple possible movements a user may be performing.

As discussed above, the sensor data obtained at act 302 may be obtained by recording sensor signals as each of one or multiple users performs each of one or more tasks one or more multiple times. As the user(s) perform the task(s), position information describing the spatial position of different body segments during performance of the task(s) may be obtained in act 304. In some embodiments, the position information is obtained using one or more external devices or systems that track the position of different points on the body during performance of a task. For example, a motion capture system, a laser scanner, a device to measure mutual magnetic induction, or some other system configured to capture position information may be used. As one non-limiting example, a plurality of position sensors may be placed on segments of the fingers of the right hand and a motion capture system may be used to determine the spatial location of each of the position sensors as the user performs a task such as grasping an object. The sensor data obtained at act 302 may be recorded simultaneously with recording of the position information obtained in act 804. In this example, position information indicating the position of each finger segment over time as the grasping motion is performed is obtained.

Next, process 300 proceeds to act 306, where the sensor signals obtained in act 302 and/or the position information obtained in act 304 are optionally processed. For example, the sensor signals or the position information signals may be processed using amplification, filtering, rectification, or other types of signal processing.

Next, process 300 proceeds to act 308, where musculoskeletal position characteristics are determined based on the position information (as collected in act 304 or as processed in act 306). In some embodiments, rather than using recorded spatial (e.g., x, y, z) coordinates corresponding to the position sensors as training data to train the statistical model, a set of derived musculoskeletal position characteristic values are determined based on the recorded position information, and the derived values are used as training data for training the statistical model. For example, using information about the constraints between connected pairs of rigid segments in the articulated rigid body model, the position information may be used to determine joint angles that define angles between each connected pair of rigid segments at each of multiple time points during performance of a task. Accordingly, the position information obtained in act 304 may be represented by a vector of n joint angles at each of a plurality of time points, where n is the number of joints or connections between segments in the articulated rigid body model.

Next, process 300 proceeds to act 310, where the time series information obtained at acts 302 and 308 is combined to create training data used for training a statistical model at act 310. The obtained data may be combined in any suitable way. In some embodiments, each of the sensor signals obtained at act 302 may be associated with a task or movement within a task corresponding to the musculoskeletal position characteristics (e.g., joint angles) determined based on the positional information recorded in act 304 as the user performed the task or movement. In this way, the sensor signals may be associated with musculoskeletal position characteristics (e.g., joint angles) and the statistical model may be trained to predict that the musculoskeletal representation will be characterized by particular musculoskeletal position characteristics between different body segments when particular sensor signals are recorded during performance of a particular task.

In embodiments comprising sensors of different types (e.g., IMU sensors and neuromuscular sensors) configured to simultaneously record different types of movement information during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the statistical model corresponds to time series data at the same time resolution. Resampling at least some of the sensor data may be performed in any suitable way including, but not limited to using interpolation for upsampling and using decimation for downsampling.

In addition to or as an alternative to resampling at least some of the sensor data when recorded at different sampling rates, some embodiments employ a statistical model configured to accept multiple inputs asynchronously. For example, the statistical model may be configured to model the distribution of the "missing" values in the input data having a lower sampling rate. Alternatively, the timing of training of the statistical model occur asynchronously as input from multiple sensor data measurements becomes available as training data.

Next, process 300 proceeds to act 312, where a statistical model for predicting musculoskeletal position information is trained using the training data generated at act 310. The statistical model being trained may take as input a sequence of data sets each of the data sets in the sequence comprising an n-dimensional vector of sensor data. The statistical model may provide output that indicates, for each of one or more tasks or movements that may be performed by a user, the likelihood that the musculoskeletal representation of the user's body will be characterized by a set of musculoskeletal position characteristics (e.g., a set of joint angles between segments in an articulated multi-segment body model). For example, the statistical model may take as input a sequence of vectors $\{x_k | 1 \leq k \leq K\}$ generated using measurements obtained at time points $t_1, t_2, \ldots, t_K$, where the ith component of vector xj is a value measured by the ith sensor at time $t_j$ and/or derived from the value measured by the ith sensor at time $t_j$. In another non-limiting example, a derived value provided as input to the statistical model may comprise features extracted from the data from all or a subset of the sensors at and/or prior to time $t_j$ (e.g., a covariance matrix, a power spectrum, a combination thereof, or any other suitable derived representation). Based on such input, the statistical model may provide output indicating, a probability that a musculoskeletal representation of the user's body will be characterized by a set of musculoskeletal position characteristics. As one non-limiting example, the statistical model may be trained to predict a set of joint angles for segments in the fingers in the hand over time as a user grasps an object. In this example, the trained statistical model may output, a set of predicted joint angles for joints in the hand corresponding to the sensor input.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a variational autoencoder, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some of the embodiments in which the statistical model is a neural network, the output layer of the neural network may provide a set of output values corresponding to a respective set of possible musculoskeletal position characteristics (e.g., joint angles). In this way, the neural network may operate as a non-linear regression model configured to predict musculoskeletal position characteristics from raw or pre-processed sensor measurements. It should be appreciated that, in some embodiments, any other suitable non-linear regression model may be used instead of a neural network, as aspects of the technology described herein are not limited in this respect.

In some embodiments, the neural network can be implemented based on a variety of topologies and/or architectures including deep neural networks with fully connected (dense) layers, Long Short-Term Memory (LSTM) layers, convolutional layers, Temporal Convolutional Layers (TCL), or other suitable type of deep neural network topology and/or architecture. The neural network can have different types of output layers including output layers with logistic sigmoid activation functions, hyperbolic tangent activation functions, linear units, rectified linear units, or other suitable type of nonlinear unit. Likewise, the neural network can be configured to represent the probability distribution over n different classes via, for example, a softmax function or include an output layer that provides a parameterized distribution e.g., mean and variance of a Gaussian distribution.

It should be appreciated that aspects of the technology described herein are not limited to using neural networks, as other types of statistical models may be employed in some embodiments. For example, in some embodiments, the statistical model may comprise a hidden Markov model, a Markov switching model with the switching allowing for toggling among different dynamic systems, dynamic Bayesian networks, and/or any other suitable graphical model having a temporal component. Any such statistical model may be trained at act 312 using the sensor data obtained at act 302.

As another example, in some embodiments, the statistical model may take as input, features derived from the sensor data obtained at act 302. In such embodiments, the statistical model may be trained at act 312 using features extracted from the sensor data obtained at act 302. The statistical model may be a support vector machine, a Gaussian mixture model, a regression based classifier, a decision tree classifier, a Bayesian classifier, and/or any other suitable classifier, as aspects of the technology described herein are not limited in this respect. Input features to be provided as training data to the statistical model may be derived from the sensor data obtained at act 302 in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the statistical model.

In some embodiments, at act 312, values for parameters of the statistical model may be estimated from the training data generated at act 310. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

Next, process 300 proceeds to act 314, where the trained statistical model is stored (e.g., in datastore—not shown). The trained statistical model may be stored using any suitable format, as aspects of the technology described herein are not limited in this respect. In this way, the statistical model generated during execution of process 300 may be used at a later time, for example, to predict musculoskeletal position information (e.g., joint angles) for a given set of input sensor data, as described below.

In some embodiments, sensor signals are recorded from a plurality of sensors (e.g., arranged on or near the surface of a user's body) that record activity associated with movements of the body during performance of a task. The recorded signals may be optionally processed and provided as input to a statistical model trained using one or more techniques described above in connection with FIG. 3. In some embodiments that continuously record autonomous signals, the continuously recorded signals (raw or processed) may be continuously or periodically provided as input to the trained statistical model for prediction of musculoskeletal position information (e.g., joint angles) for the given set of input sensor data. As discussed above, in some embodiments, the trained statistical model is a user-independent model trained based on autonomous sensor and position information measurements from a plurality of users. In other embodiments, the trained model is a user-dependent model trained on data recorded from the individual user from which the data associated with the sensor signals is also acquired.

After the trained statistical model receives the sensor data as a set of input parameters, the predicted musculoskeletal position information is output from the trained statistical model. As discussed above, in some embodiments, the predicted musculoskeletal position information may comprise a set of musculoskeletal position information values (e.g., a set of joint angles) for a multi-segment articulated rigid body model representing at least a portion of the user's body. In other embodiments, the musculoskeletal position information may comprise a set of probabilities that the user is performing one or more movements from a set of possible movements.

In some embodiments, after musculoskeletal position information is predicted, a computer-based musculoskeletal representation of the user's body is generated based, at least in part, on the musculoskeletal position information output from the trained statistical model. The computer-based musculoskeletal representation may be generated in any suitable way. For example, a computer-based musculoskeletal model of the human body may include multiple rigid body segments, each of which corresponds to one or more skeletal structures in the body. For example, the upper arm may be represented by a first rigid body segment, the lower arm may be represented by a second rigid body segment the palm of the hand may be represented by a third rigid body segment, and each of the fingers on the hand may be represented by at least one rigid body segment (e.g., at least fourth-eighth rigid body segments). A set of joint angles between connected rigid body segments in the musculoskeletal model may define the orientation of each of the connected rigid body segments relative to each other and a reference frame, such as the torso of the body. As new sensor data is measured and processed by the statistical model to provide new predictions of the musculoskeletal position information (e.g., an updated set of joint angles), the computer-based musculoskeletal representation of the user's body may be updated based on the updated set of joint angles determined based on the output of the statistical model. In this way the computer-based musculoskeletal representation is dynamically updated in real-time as sensor data is continuously recorded.

The computer-based musculoskeletal representation may be represented and stored in any suitable way, as embodiments of the technology described herein are not limited with regard to the particular manner in which the representation is stored. Additionally, although referred to herein as a "musculoskeletal" representation, to reflect that muscle activity may be associated with the representation in some embodiments, as discussed in more detail below, it should be appreciated that some musculoskeletal representations used in accordance with some embodiments may correspond to skeletal structures, muscular structures or a combination of skeletal structures and muscular structures in the body.

In some embodiments, direct measurement of neuromuscular activity and/or muscle activity underlying the user's movements may be combined with the generated musculoskeletal representation. Measurements from a plurality of sensors placed at locations on a user's body may be used to create a unified representation of muscle recruitment by superimposing the measurements onto a dynamically-posed skeleton. In some embodiments, muscle activity sensed by neuromuscular sensors and/or information derived from the muscle activity (e.g., force information) may be combined with the computer-generated musculoskeletal representation in real time.

Figure 4A:
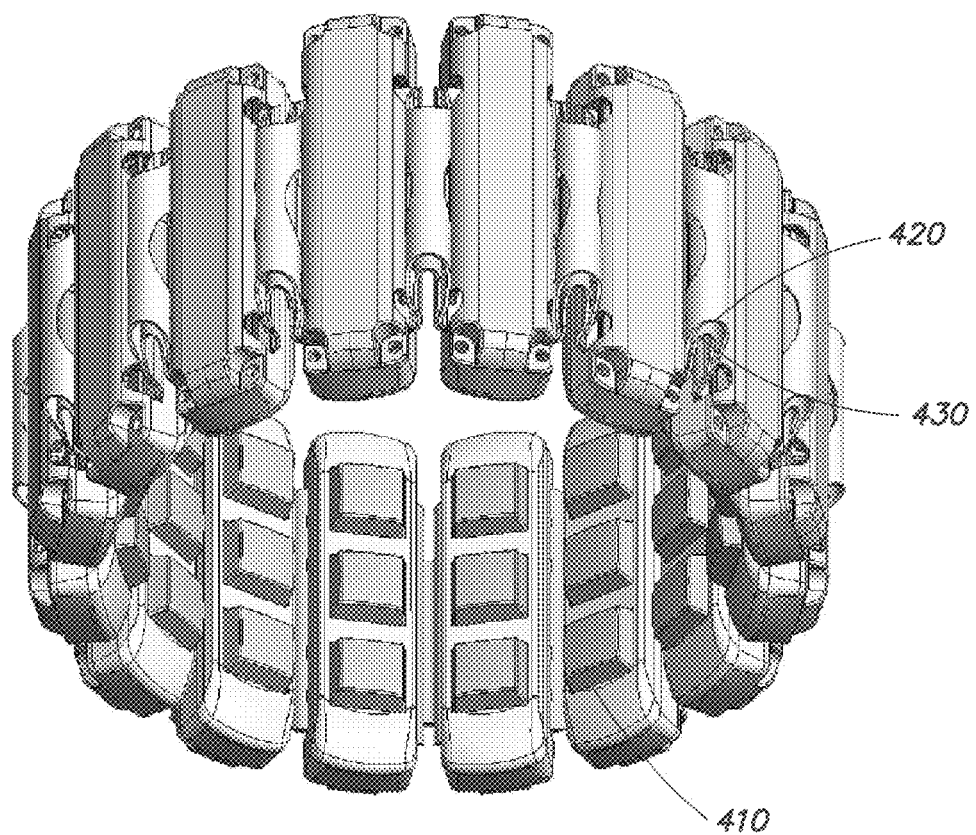
FIG. 4A illustrates a wearable system with sixteen EMG sensors arranged circumferentially around an elastic band configured to be worn around a user's lower arm or wrist, in accordance with some embodiments of the technology described herein.

FIG. 4A illustrates a wearable system with sixteen neuromuscular sensors 410 (e.g., EMG sensors) arranged circumferentially around an elastic band 420 configured to be worn around a user's lower arm or wrist. As shown, EMG sensors 410 are arranged circumferentially around elastic band 420. It should be appreciated that any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task.

Figure 4B:
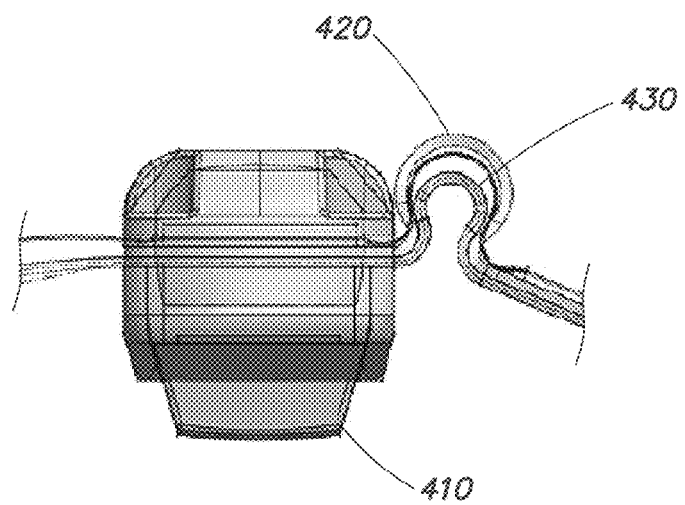
FIG. 4B is a cross-sectional view through one of the sixteen EMG sensors illustrated in FIG. 4A.

In some embodiments, sensors 410 include a set of neuromuscular sensors (e.g., EMG sensors). In other embodiments, sensors 410 can include a set of neuromuscular sensors and at least one "auxiliary" sensor configured to continuously record auxiliary signals. Examples of auxiliary sensors include, but are not limited to, other sensors such as IMU sensors, microphones, imaging sensors (e.g., a camera), radiation based sensors for use with a radiation-generation device (e.g., a laser-scanning device), or other types of sensors such as a heart-rate monitor. As shown the sensors 410 may be coupled together using flexible electronics 430 incorporated into the wearable device. FIG. 4B illustrates a cross-sectional view through one of the sensors 410 of the wearable device shown in FIG. 4A.

Figure 5A:
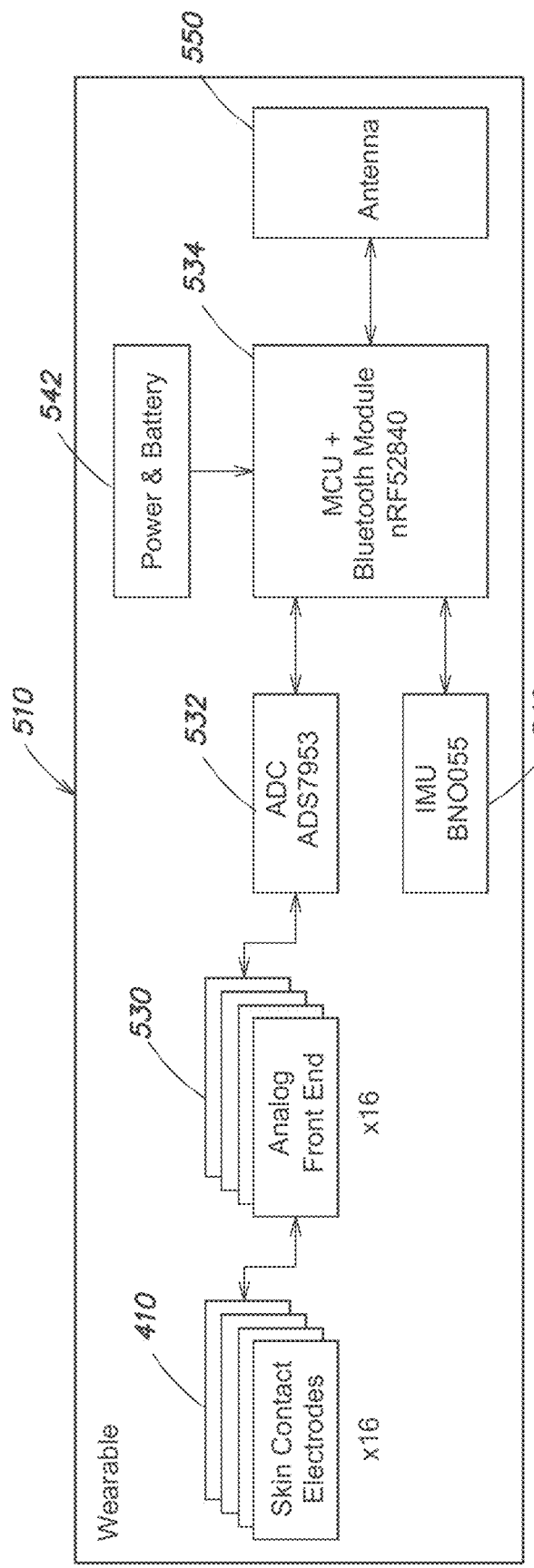
FIGS. 5A and 5B schematically illustrate components of a computer-based system on which some embodiments are implemented.
Figure 5B:
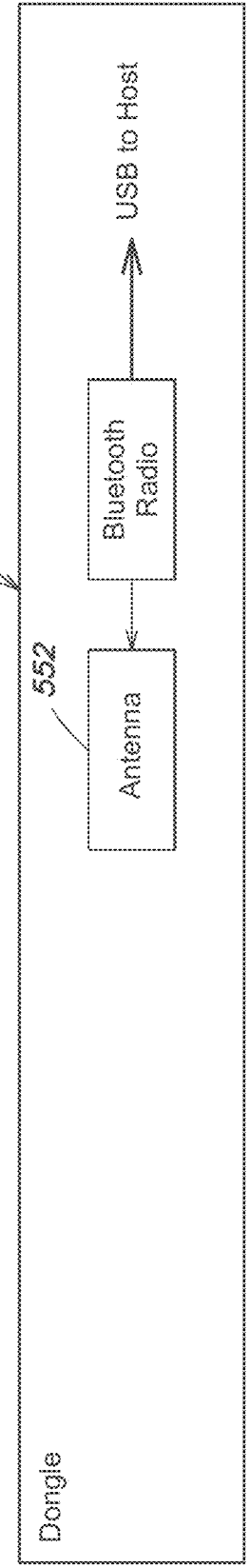

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 410 are discussed in more detail below in connection with FIGS. 5A and 5B FIGS. 5A and 5B illustrate a schematic diagram with internal components of a wearable system with sixteen EMG sensors, in accordance with some embodiments of the technology described herein. As shown, the wearable system includes a wearable portion 510 (FIG. 5A) and a dongle portion 520 (FIG. 5B) in communication with the wearable portion 510 (e.g., via Bluetooth or another suitable short range wireless communication technology). As shown in FIG. 5A, the wearable portion 510 includes the sensors 410, examples of which are described in connection with FIGS. 4A and 4B. The output of the sensors 410 is provided to analog front end 530 configured to perform analog processing (e.g., noise reduction, filtering, etc.) on the recorded signals. The processed analog signals are then provided to analog-to-digital converter 532, which converts the analog signals to digital signals that can be processed by one or more computer processors. An example of a computer processor that may be used in accordance with some embodiments is microcontroller (MCU) 534 illustrated in FIG. 5A. As shown, MCU 534 may also include inputs from other sensors (e.g., IMU sensor 540), and power and battery module 542. The output of the processing performed by MCU may be provided to antenna 550 for transmission to dongle portion 520 shown in FIG. 5B.

Dongle portion 520 includes antenna 552 configured to communicate with antenna 550 included as part of wearable portion 510. Communication between antenna 550 and 552 may occur using any suitable wireless technology and protocol, non-limiting examples of which include radiofrequency signaling and Bluetooth. As shown, the signals received by antenna 552 of dongle portion 520 may be provided to a host computer for further processing, display, and/or for effecting control of a particular physical or virtual object or objects.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

In addition to the description above, this disclosure includes the description in Appendices A and B attached hereto, which are incorporated by reference.

What is claimed is:

1. A computerized system comprising:
at least one computer processor programmed to:
generate a musculoskeletal representation based, at least in part, on a first plurality of neuromuscular signals recorded using one or more sensors attached to a user's body, wherein the musculoskeletal representation is generated based at least in part on:
position information describing a spatial relationship between two or more connected segments of the musculoskeletal representation, wherein the position information is determined based, at least in part, on the first plurality of neuromuscular signals, and
force information describing a first amount of force exerted by at least one segment of the musculoskeletal representation, wherein the force information is determined based, at least in part, on the first plurality of neuromuscular signals,
wherein a first portion of the user's body has at least one of the one or more sensors attached thereto and wherein a second portion of the user's body lacks an attached sensor, and
wherein a handstate of the second portion of the user's body having no sensor attached is predicted using the position information and force information from the one or more sensors on the first portion of the user's body and further based on one or more constraints indicating how the first and second portions of the user's body are connected;
determine that at least an identified portion of the handstate represents a specific type of gesture, the determining including reducing a dimensionality associated with the generated musculoskeletal representation to reduce latency upon rendering, wherein reducing the dimensionality is performed by a statistical model configured to select an appropriate sub-manifold of the generated musculoskeletal representation; and
render, via a user interface, a visual representation based on the generated musculoskeletal representation, the generated musculoskeletal representation including the first and second portions of the user's body, wherein the visual representation includes a visual indication of the position information and a visual indication of the force information, wherein upon determining that that the identified portion of the handstate represents the specified type of gesture, the specified type of gesture is rendered with a higher level of fidelity that is to be used with gestures of the specified type.

2. The computerized system of claim 1, wherein the at least one computer processor is further programmed to:
update the musculoskeletal representation based, at least in part, on a second plurality of neuromuscular signals recorded from the one or more sensors attached to the user's body, wherein updating the musculoskeletal representation comprises updating the position information and the force information, wherein the updated force information describes a second amount of force exerted by the at least one segment of the musculoskeletal representation; and
update in real time the visual representation based on the updated musculoskeletal representation, wherein updating the visual representation comprises updating the visual indication of the force information based on the updated force information,
wherein updating the visual indication of the force information comprises changing a color of a portion of the visual representation corresponding to the at least one segment of the updated musculoskeletal representation to indicate the updated force information.

3. The computerized system of claim 2, wherein changing the color comprises changing a hue of the color for the portion of the visual representation corresponding to the at least one segment, and wherein the hue is indicative of the second amount of force exerted by the at least one segment.

4. The computerized system of claim 2, wherein updating the visual indication of the force information comprises changing a scale or size of a portion of the visual representation corresponding to the at least one segment of the updated musculoskeletal representation to indicate the updated force information.

5. The computerized system of claim 2, wherein updating the visual indication of the force information comprises applying at least one visual element to a portion of the visual representation corresponding to the at least one segment of the updated musculoskeletal representation to indicate the updated force information.

6. The computerized system of claim 5, wherein a change in a characteristic of the at least one visual element is indicative of the second amount of force exerted by the at least one segment.

7. The computerized system of claim 2, wherein updating the visual indication of the force information comprises increasing or decreasing a brightness of a portion of the visual representation corresponding to the at least one segment of the updated musculoskeletal representation to indicate the updated force information.

8. The computerized system of claim 7, wherein a degree of increase or decrease in the brightness is indicative of the second amount of force exerted by the at least one segment.

9. The computerized system of claim 2, wherein the at least one computer processor is further programmed to:
output a sound representation indicative of the updated force information associated with the updated musculoskeletal representation.

10. The computerized system of claim 2, wherein the at least one computer processor is further programmed to:
execute a computer application that provides a virtual reality environment; and
update in real time the visual representation in the virtual reality environment, wherein updating the visual representation further comprises updating the visual indication of the position information and the visual indication of the force information.

11. The computerized system of claim 10, wherein the virtual reality environment comprises a virtual object, and wherein updating the visual representation comprises updating the visual representation such that a hand interacts with the virtual object within the virtual reality environment.

12. The computerized system of claim 11, wherein updating the visual indication of the force information comprises changing an appearance or dimension of the virtual object, wherein a degree of change of the virtual object indicates the second amount of force exerted by the at least one segment when interacting with the virtual object within the virtual reality environment.

13. The computerized system of claim 12, wherein interacting with the virtual object comprises an action selected from the group consisting of grasping the virtual object, dropping the virtual object, pushing the virtual object, throwing the virtual object, pulling the virtual object, opening the virtual object, and closing the virtual object.

14. The computerized system of claim 10, wherein the virtual reality environment comprises a shared virtual reality environment, and wherein the at least one computer processor is further programmed to provide the updated visual representation to a third-party participating in the shared virtual reality environment.

15. The computerized system of claim 14, wherein providing the updated visual representation comprises providing the updated visual indication of the position information and the updated visual indication of the force information.

16. The computerized system of claim 1, wherein the at least one computer processor is further programmed to:
provide feedback regarding the first amount of force and/or the second amount of force exerted by the at least one segment of the musculoskeletal representation.

17. The computerized system of claim 16, wherein providing feedback comprises providing haptic feedback indicative of the first amount of force and/or the second amount of force exerted by the at least one segment.

18. The computerized system of claim 16, wherein providing feedback comprises providing feedback to a user in a virtual reality environment.

19. The computerized system of claim 16, wherein providing feedback comprises providing feedback to a third-party in a shared virtual reality environment.

20. A method comprising:
generating the musculoskeletal representation based, at least in part, on a plurality of neuromuscular signals recorded using one or more sensors attached to a user's body, wherein the musculoskeletal representation is generated based at least in part on:
position information describing a spatial relationship between two or more connected segments of the musculoskeletal representation, wherein the position information is determined based, at least in part, on the plurality of neuromuscular signals, and
force information describing a first amount of force exerted by at least one segment of the musculoskeletal representation, wherein the force information is determined based, at least in part, on the plurality of neuromuscular signals,
wherein a first portion of the user's body has at least one of the one or more sensors attached thereto and wherein a second portion of the user's body lacks an attached sensor, and
wherein a handstate of the second portion of the user's body having no sensor attached is predicted using the position information and force information from the one or more sensors on the first portion of the user's body and further based on one or more constraints indicating how the first and second portions of the user's body are connected;
determining that at least an identified portion of the handstate represents a specific type of gesture, the determining including reducing a dimensionality associated with the generated musculoskeletal representation to reduce latency upon rendering, wherein reducing the dimensionality is performed by a statistical model configured to select an appropriate sub-manifold of the generated musculoskeletal representation; and rendering, via a user interface, the visual representation based on the generated musculoskeletal representation, the generated musculoskeletal representation including the first and second portions of the user's body, wherein the visual representation includes a visual indication of the position information and a visual indication of the force information, wherein upon determining that that the identified portion of the handstate represents the specified type of gesture, the specified type of gesture is rendered with a higher level of fidelity that is to be used with gestures of the specified type.

21. The method of claim 20, further comprising:
updating in real time the visual representation in a virtual reality environment, wherein updating the visual representation further comprises updating the visual indication of the position information and the visual indication of the force information.

22. The method of claim 21, wherein the virtual reality environment comprises a shared virtual reality environment, and wherein the method further comprises providing the updated visual representation to a third-party participating in the shared virtual reality environment.

23. The method of claim 22, wherein providing the updated visual representation comprises providing the updated visual indication of the position information and the updated visual indication of the force information.

24. The method of claim 20, further comprising:
providing feedback regarding the first amount of force and/or the second amount of force exerted by the at least one segment of the musculoskeletal representation.

25. The method of claim 24, wherein providing feedback comprises providing haptic feedback indicative of the first amount of force and/or the second amount of force exerted by the at least one segment.

26. The method of claim 24, wherein providing feedback comprises providing feedback to a user in a virtual reality environment or providing feedback to a third-party in a shared virtual reality environment.

27. A non-transitory computer-readable medium encoded with a plurality of instructions that, when executed by at least one computer processor performs a method of:
generating a musculoskeletal representation based, at least in part, on a plurality of neuromuscular signals recorded using one or more sensors attached to a user's body, wherein the musculoskeletal representation is generated based at least in part on:
position information describing a spatial relationship between two or more connected segments of the musculoskeletal representation, wherein the position information is determined based, at least in part, on the plurality of neuromuscular signals, and
force information describing a first amount of force exerted by at least one segment of the musculoskeletal representation, wherein the force information is determined based, at least in part, on the plurality of neuromuscular signals,
wherein a first portion of the user's body has at least one of the one or more sensors attached thereto and wherein a second portion of the user's body lacks an attached sensor, and
wherein a handstate of the second portion of the user's body having no sensor attached is predicted using the position information and force information from the one or more sensors on the first portion of the user's body and further based on one or more constraints indicating how the first and second portions of the user's body are connected;
determining that at least an identified portion of the handstate represents a specific type of gesture, the determining including reducing a dimensionality associated with the generated musculoskeletal representation to reduce latency upon rendering, wherein reducing the dimensionality is performed by a statistical model configured to select an appropriate sub-manifold of the generated musculoskeletal representation; and
rendering, via a user interface, a visual representation based on the generated musculoskeletal representation, the generated musculoskeletal representation including the first and second portions of the user's body, wherein the visual representation includes a visual indication of the position information and a visual indication of the force information, wherein upon determining that that the identified portion of the handstate represents the specified type of gesture, the specified type of gesture is rendered with a higher level of fidelity that is to be used with gestures of the specified type.

28. The non-transitory computer-readable medium of claim 27, wherein the method further comprises:
updating in real time the visual representation in a virtual reality environment, wherein updating the visual representation further comprises updating the visual indication of the position information and the visual indication of the force information.

29. The non-transitory computer-readable medium of claim 28, wherein the virtual reality environment comprises a shared virtual reality environment, and wherein the method further comprises providing the updated visual representation to a third-party participating in the shared virtual reality environment.

30. The computerized system of claim 1, wherein:
the at least one segment of the musculoskeletal representation comprises a first segment and a second segment, and
the musculoskeletal representation is generated based on force information describing the first amount of force and a second amount of force exerted by the first segment and a third amount of force exerted by the second segment.

* * * * *